US012789010B2

(12) United States Patent
Takayanagi et al.

(10) Patent No.: US 12,789,010 B2
(45) Date of Patent: Nov. 10, 2026

(54) TREATMENT PLANNING SYSTEM, METHOD, AND PROGRAM

(71) Applicants: Hitachi, Ltd., Tokyo (JP); NATIONAL UNIVERSITY CORPORATION HOKKAIDO UNIVERSITY, Sapporo (JP)

(72) Inventors: Taisuke Takayanagi, Tokyo (JP); Takahiro Yamada, Tokyo (JP); Shusuke Hirayama, Tokyo (JP); Koichi Miyazaki, Tokyo (JP); Keiji Kobashi, Sapporo (JP); Hidefumi Aoyama, Sapporo (JP); Takayuki Hashimoto, Sapporo (JP); Norio Katoh, Sapporo (JP); Hiroshi Taguchi, Sapporo (JP); Koichi Yasuda, Sapporo (JP); Yasuhito Onodera, Sapporo (JP)

(73) Assignees: HITACHI, LTD., Tokyo (JP); NATIONAL UNIVERSITY CORPORATION HOKKAIDO UNIVERSITY, Sapporo (JP)

( * ) Notice: Subject to any disclaimer, the term of this patent is extended or adjusted under 35 U.S.C. 154(b) by 518 days.

(21) Appl. No.: 18/375,597

(22) Filed: Oct. 2, 2023

(65) Prior Publication Data

US 2024/0285972 A1 Aug. 29, 2024

(30) Foreign Application Priority Data

Feb. 28, 2023 (JP) ................................ 2023-030506

(51) Int. Cl.
*A61N 5/10* (2006.01)

(52) U.S. Cl.
CPC ......... *A61N 5/1038* (2013.01); *A61N 5/1064* (2013.01); *A61N 2005/1092* (2013.01)

(58) Field of Classification Search
None
See application file for complete search history.

(56) References Cited

U.S. PATENT DOCUMENTS

2020/0069968 A1 3/2020 Kobashi et al.
2022/0296925 A1* 9/2022 Wedenberg .......... A61N 5/1038
(Continued)

FOREIGN PATENT DOCUMENTS

WO 2018116354 A1 6/2018
WO 2021/213818 A1 10/2021

OTHER PUBLICATIONS

Japanese Office Action received in corresponding Japanese Application No. 2023-030506 dated Mar. 24, 2026.
(Continued)

*Primary Examiner* — Hoon K Song
(74) *Attorney, Agent, or Firm* — Mattingly & Malur, PC

(57) ABSTRACT

A treatment planning system is configured to create a treatment planning for radiotherapy and includes a processing device and a memory. The memory stores a plurality of calculation models, and the processing device uses at least two of the plurality of calculation models to calculate calculation values of biological effect indices representing an effect of radiotherapy with respect to a condition for radiotherapy, and searches for the condition so that at least two of the calculation values to be calculated approach a predetermined target value.

12 Claims, 6 Drawing Sheets

(56) References Cited

U.S. PATENT DOCUMENTS

| | | | | |
|---|---|---|---|---|
| 2023/0211177 | A1 | 7/2023 | Janson et al. | |
| 2025/0090868 | A1* | 3/2025 | Liu | A61N 5/103 |

OTHER PUBLICATIONS

Joe H. Chang, et al., "RADBIOMOD: A simple program for utilising biological modelling in radiotherapy plan evaluation", Physica Medica 32, 248-254, 2015.

C. M. van Leeuwen, et al., "The alfa and beta of tumours: a review of parameters of the linear-quadratic model, derived from clinical radiotherapy studies", Radiation Oncology (2018) 13:96, pp. 1-11.

* cited by examiner

TREATMENT PLANNING SYSTEM, METHOD, AND PROGRAM

CROSS-REFERENCE TO RELATED APPLICATION

The present application claims priority from Japanese application JP2023-030506, filed on Feb. 28, 2023, the content of which is hereby incorporated by reference into this application.

BACKGROUND OF THE INVENTION

1. Field of the Invention

The present disclosure relates to a technique for creating a treatment planning for radiotherapy.

2. Description of the Related Art

In radiotherapy, a biological effect index, which is a predictive index of treatment prognosis, is used. As biological effect indices, a tumor control probability (TCP) and a normal tissue complication probability (NTCP) are often used.

WO2018/116354A1 discloses a treatment planning method in which a TCP and an NTCP are calculated based on a calculation model using a prescription (a total dose, a fraction number, etc.) as an input, and the prescription is optimized so that the TCP and the NTCP are brought close to target values. In this case, it is determined that the closer the TCP is to 1, and the closer the NTCP is to 0, the better the prescription.

A plurality of calculation models for calculating a TCP are proposed in Non-Patent Literature 1 "J. H. Chang et al., RADBIOMOD: A simple program for utilising biological modelling in radiotherapy plan evaluation, Physica Medica 32, 248-254, 2016". A Poisson statistical model will be described as an example from among them. In general, it is known that cell death caused by radiation follows Poisson statistics. Assuming that the number of cancer cells contained in a tumor (target) before the start of treatment is n and the survival probability of a cancer cell associated with radiotherapy is λ, the probability P (χ=0) that the number χ of cancer cells in the target is 0 after the end of the treatment, that is, the TCP is expressed by Equation (1).

[Equation 1]

$$TCP = P(\chi = 0) = \frac{\exp\{-n\lambda\}(n\lambda)^{\chi}}{\chi!} = \exp\{-n\lambda\} \tag{1}$$

In this case, the survival probability λ of a tumor cell associated with radiotherapy is expressed by a linear-quadratic curve model (LQ model) as in Equation (2).

[Equation 2]

$$\lambda = \exp\left\{-\alpha D\left(1 + \frac{\beta}{N\alpha}D\right)\right\} \tag{2}$$

In Equation (2), D is the total irradiation dose to the target, and N is the number of times that fractionated irradiation with radiation is performed. α and β are parameters indicating radiosensitivity of cancer cells. α and β can be determined by an in vitro radiation irradiation experiment or the like. The α and β are not uniquely determined, and even in a similar case, different numerical values may be adopted depending on documents and facilities.

In addition, in a calculation model (for example, an equivalent uniform dose model or the like) different from the above-described Poisson statistical model, other parameters may be used instead of α and β. Other parameters can be determined, for example, by fitting a calculation model to a graph in which a vertical axis represents past treatment results (for example, 1 for no exacerbation and 0 for exacerbation), a horizontal axis represents an equivalent uniform dose (EUD) of a target, and the like.

Non-Patent Literature 2 is "C M. van Leeuwen, et al., The alfa and beta of tumours: a review of parameters of the linear-quadratic model, derived from clinical radiotherapeutic studies. Radiat Oncol. 13, 96, 2018".

SUMMARY OF THE INVENTION

As described above, there are multiple calculation models and parameter sets that may be used for the same case. Certainly, values of biological effect indices, such as the TCP or the NTCP, that are calculated by using a calculation model and a parameter set are different. Therefore, to create a treatment planning based on a biological effect index, a medical practitioner is required to consider and select which calculation model and parameter set to use for each patient. In addition, the medical practitioner may have difficulty in uniquely determining a calculation model and a parameter set. However, even in such cases, it is difficult for the medical practitioner to find a compromise plan between multiple calculation models and parameter sets.

One object included in the present disclosure is to provide a technology that enables creation of a treatment planning based on a plurality of calculation models.

A treatment planning system according to one aspect included in the present disclosure is a treatment planning system that is configured to create a treatment planning for radiotherapy and includes a processing device and a memory. The memory stores a plurality of calculation models, and the processing device uses at least two of the plurality of calculation models to calculate calculation values of biological effect indices representing an effect of radiotherapy with respect to a condition for radiotherapy, and searches for the condition so that at least two of the calculation values to be calculated approach a predetermined target value.

According to one aspect included in the present disclosure, it is possible to create a treatment planning based on a plurality of calculation models.

DESCRIPTION OF THE PREFERRED EMBODIMENTS

Hereinafter, embodiments of the present invention will be described with reference to the drawings.

Figure 1:
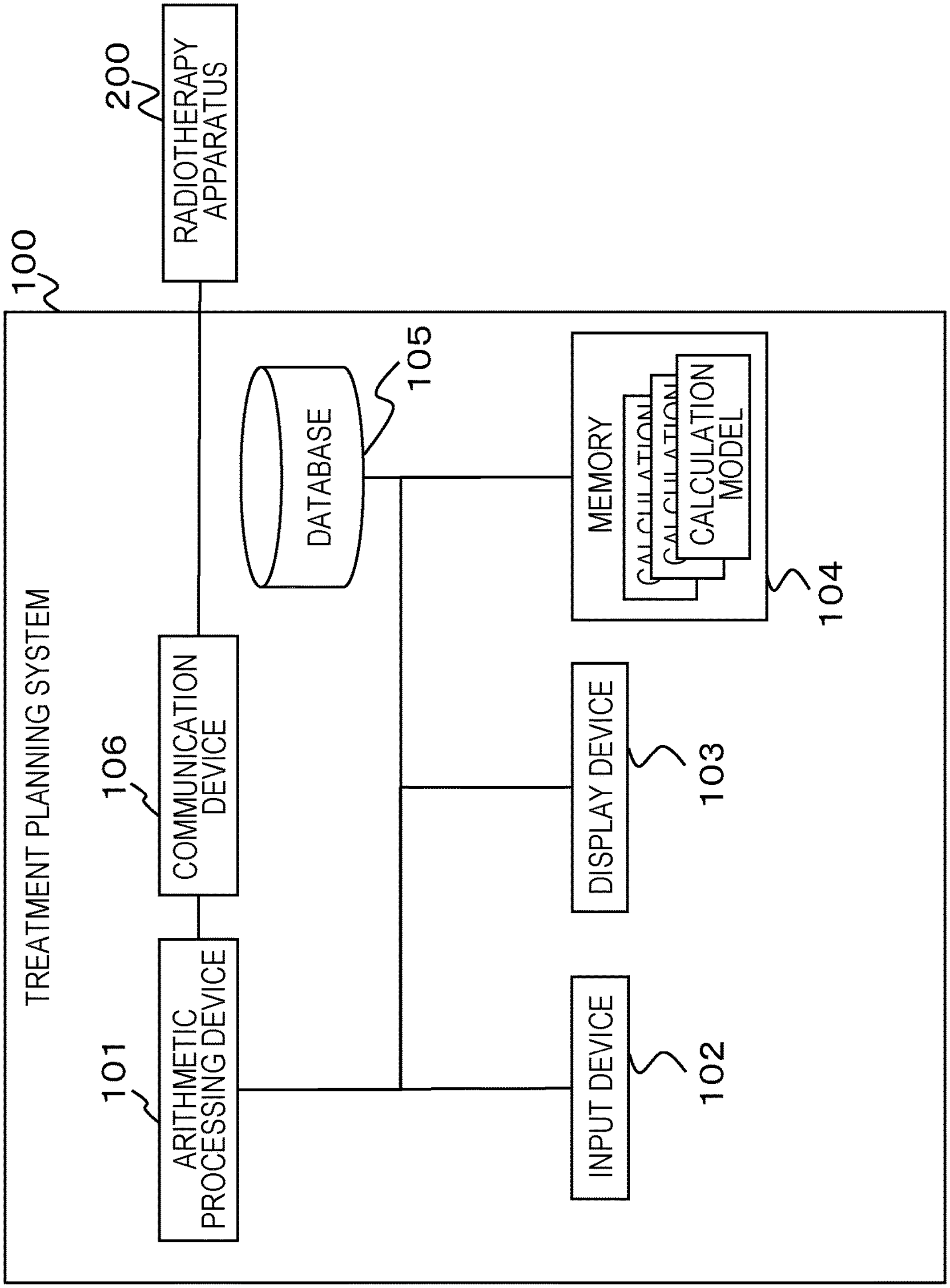
FIG. 1 is a schematic configuration diagram illustrating an example of a configuration of a treatment planning system according to the present embodiment.

FIG. 1 is a schematic configuration diagram illustrating an example of a configuration of a treatment planning system 100 according to the present embodiment. The treatment planning system 100 includes a device capable of performing various types of information processing, for example, an information processing device such as a computer device.

In the example illustrated in FIG. 1, the treatment planning system 100 includes an arithmetic processing device 101, an input device 102, a display device 103, a memory 104, a database 105, and a communication device 106. The arithmetic processing device 101 is connected to the input device 102, the display device 103, the memory 104, the database 105, and the communication device 106. This connection method is not particularly limited, and may be a connection method via a local area network (LAN) or a wide area network (WAN) such as the Internet.

The arithmetic processing device 101 is, for example, a processor such as a central processing unit (CPU), a graphic processing unit (GPU), or a field-programmable gate array (FPGA), and constitutes a control unit that controls the entire treatment planning system 100.

The input device 102 is a device that receives various types of information from an operator who operates the treatment planning system 100, and is, for example, a mouse, a keyboard, or the like. The display device 103 is a device that displays various types of information such as a treatment plan, and is, for example, a display.

The memory 104 and the database 105 are configured as the same or different recording media, and record a program (computer program) that defines the operation of the arithmetic processing device 101, and various types of information (for example, calculation models to be described later) used and generated in the arithmetic processing device 101. Examples of the recording media include a magnetic storage medium such as a hard disk drive (HDD), semiconductor storage media such as a random access memory (RAM), a read only memory (ROM), and a solid state drive (SSD), and a combination of an optical disk such as a digital versatile disk (DVD) and an optical disk drive. Note that the arithmetic processing device 101 reads the program from either one or both of the recording media at the start of the operation of the treatment planning system 100 (for example, when treatment planning system 100 is turned on), executes the read program, and executes various types of processing regarding the treatment planning, thereby controlling the entire treatment planning system 100.

The communication device 106 is a communication interface communicably connected to an external device. In the example illustrated in FIG. 1, the communication device 106 is connected to a radiotherapy apparatus 200.

In the present embodiment, an example in which the present invention is applied to a treatment planning system supporting spot scanning type particle beam therapy will be described. However, the present invention can be similarly applied to X-ray therapy or particle beam therapy other than the spot scanning method, and the same effect can be obtained. In the spot scanning method, points (spots) are three-dimensionally arranged inside and around a target region to be irradiated with radiation in a patient body, particularly a tumor or the like, and each spot is irradiated with a small-diameter beam. A prescribed dose of a beam to be emitted is determined for each spot, and when a certain spot is irradiated with a prescribed dose, the beam is deflected to the next spot, and the beam is sequentially emitted. By irradiating all the spots with a prescribed dose, a desired irradiation dose distribution is formed in the target region.

Examples of treatments other than the spot scanning method include intensity modulated radiotherapy (IMRT) using an X-ray and a treatment planning system supporting volumetric modulated arc therapy (VMAT), and the present invention is also applicable to the therapy. In an X-ray therapy apparatus that performs intensity modulation such as IMRT or VMAT, the target is irradiated with X-rays from a plurality of directions. Although the dose distribution formed in the target by X-rays emitted from each direction is not uniform, a uniform dose distribution matching the three-dimensional shape of the target is imparted to the patient body by superimposing contributions from all directions. In this case, a fluence distribution of the X-rays to be emitted from each direction can be obtained by solving an inverse problem using the treatment planning system. A multi-leaf collimator may also be placed between an x-ray source and an isocenter to obtain any fluence distribution of X-rays. Even in a treatment planning system corresponding to such a radiotherapy apparatus, the present invention can obtain an effect equivalent to the effect in the present embodiment.

Figure 2:
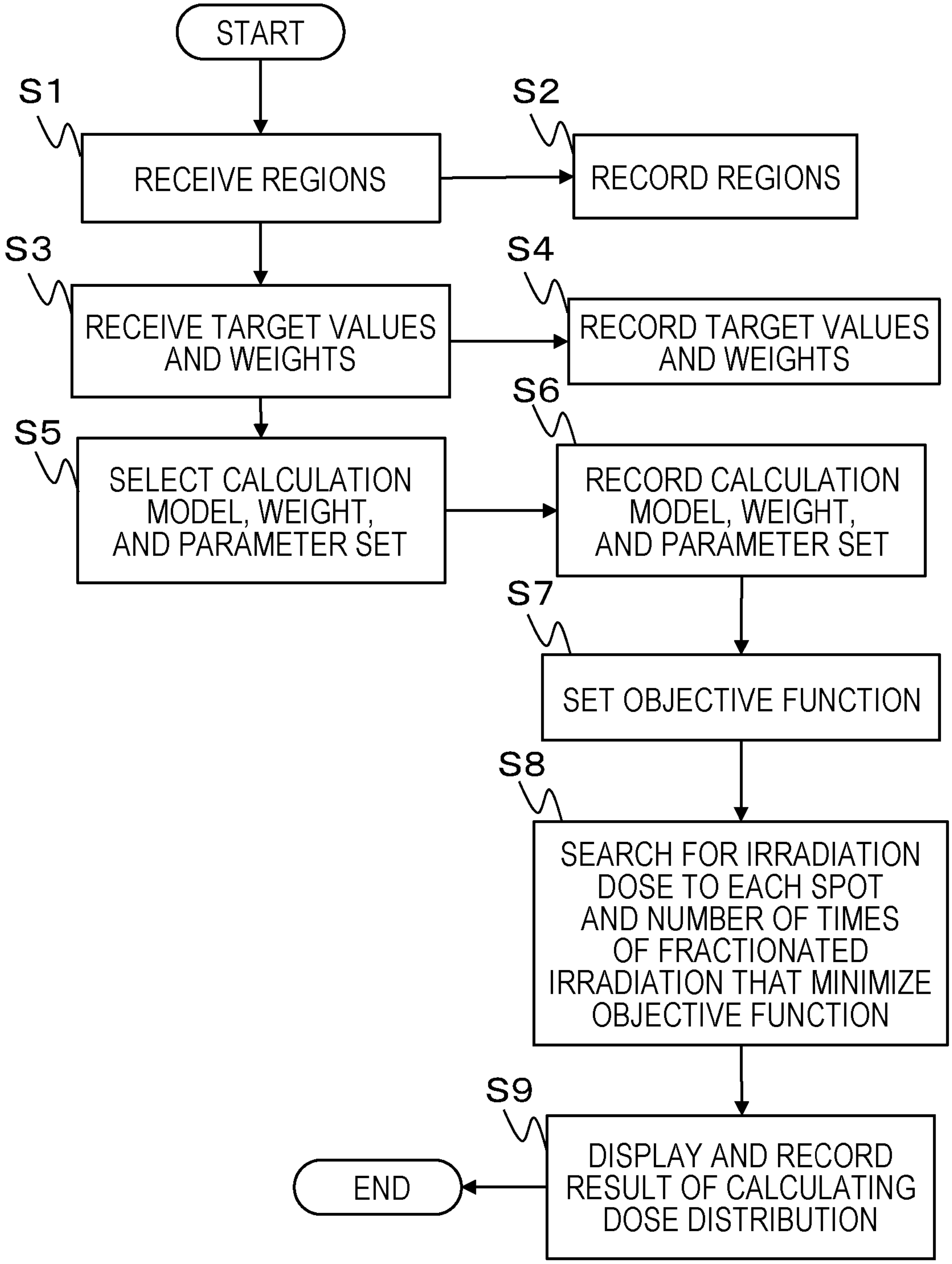
FIG. 2 is a flowchart for explaining an example of a treatment planning creation process by the treatment planning system.

FIG. 2 is a flowchart for explaining an example of a treatment planning creation process by the treatment planning system 100. A particle beam may be hereinafter referred to as radiation.

In the treatment planning creation process, first, the arithmetic processing device 101 receives a target region to be irradiated with radiation and an excluded region to be avoided from being irradiated with radiation (step S1). For example, the arithmetic processing device 101 displays each slice image of a CT image of the patient on the display device 103, and receives a target region and an excluded region for each slice image from the operator via the input device 102. The target region is, for example, a region of a tumor or the like. The excluded region is, for example, a region of an organ at risk (OAR). Hereinafter, the excluded region that is a risk region may be referred to as an OAR. In addition, both the target region and the OAR may be referred to as a region of interest.

Figure 3:
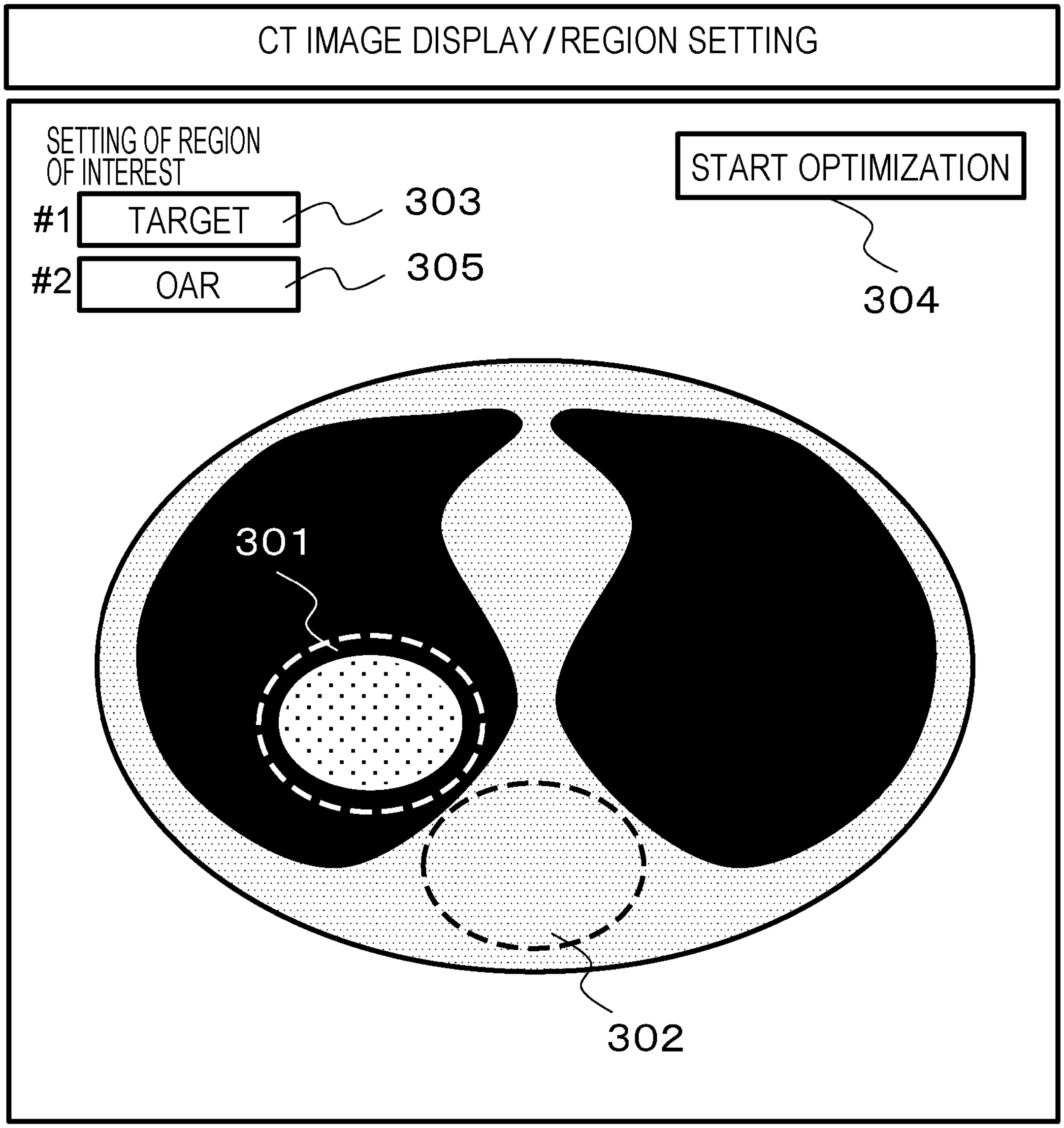
FIG. 3 is a diagram illustrating an example of a GUI for inputting a target region and an excluded region.

FIG. 3 is a diagram illustrating an example of a graphical user interface (GUI) for the operator to input the target region and the excluded region. When the operator inputs a target region 301 and an OAR 302 with a mouse, a stylus pen, or the like on a certain slice image, the target region 301 and the OAR 302 are drawn in a graphical user interface (GUI) on the display device 103 as illustrated in FIG. 3. As illustrated in FIG. 3, in the present embodiment, an example is shown in which one target region and one OAR are present, but two or more target regions and two or more OARs may be present.

The description returns to FIG. 2. The arithmetic processing device 101 records the received target region and the received excluded region in the memory 104 or the database 105 as three-dimensional position information (step S2).

Next, the arithmetic processing device 101 receives a target tumor control probability $TCP_{obj}$, which is a target value of a therapeutic effect, for the target region 301 (step S3). In addition, the arithmetic processing device 101 receives a target normal tissue complication probability $NTCP_{obj}$, which is a target value of the therapeutic effect, for the OAR 302. Furthermore, the arithmetic processing device 101 receives weights $w_{TCP}$ and $w_{NTCP}$ for the target region 301 and the OAR 302, respectively. A region of interest having a larger weight is prioritized in the optimization of the prescription.

The description returns to FIG. 2 again. The arithmetic processing device 101 records the received target tumor control probability $TCP_{obj}$, the received target normal tissue complication probability $NTCP_{obj}$, and the weights $w_{TCP}$ and $w_{NTCP}$ in the memory 104 or the database 105 (step S4).

Furthermore, the arithmetic processing device 101 receives a calculation model for calculating the TCP or the NTCP, a weight $w_{model}$ Of the calculation model, and a parameter set of the calculation model for the target region 301 and the OAR 302 (step S5). The arithmetic processing device 101 records the received calculation model, weight $w_{model}$, and parameter set in the memory 104 or the database 105 (step S6). Similarly to the weights $w_{TCP}$ and $w_{NTCP}$, when a plurality of calculation models are set, a calculation model with a larger weight $w_{model}$ is prioritized in the optimization of the prescription.

Figure 4:
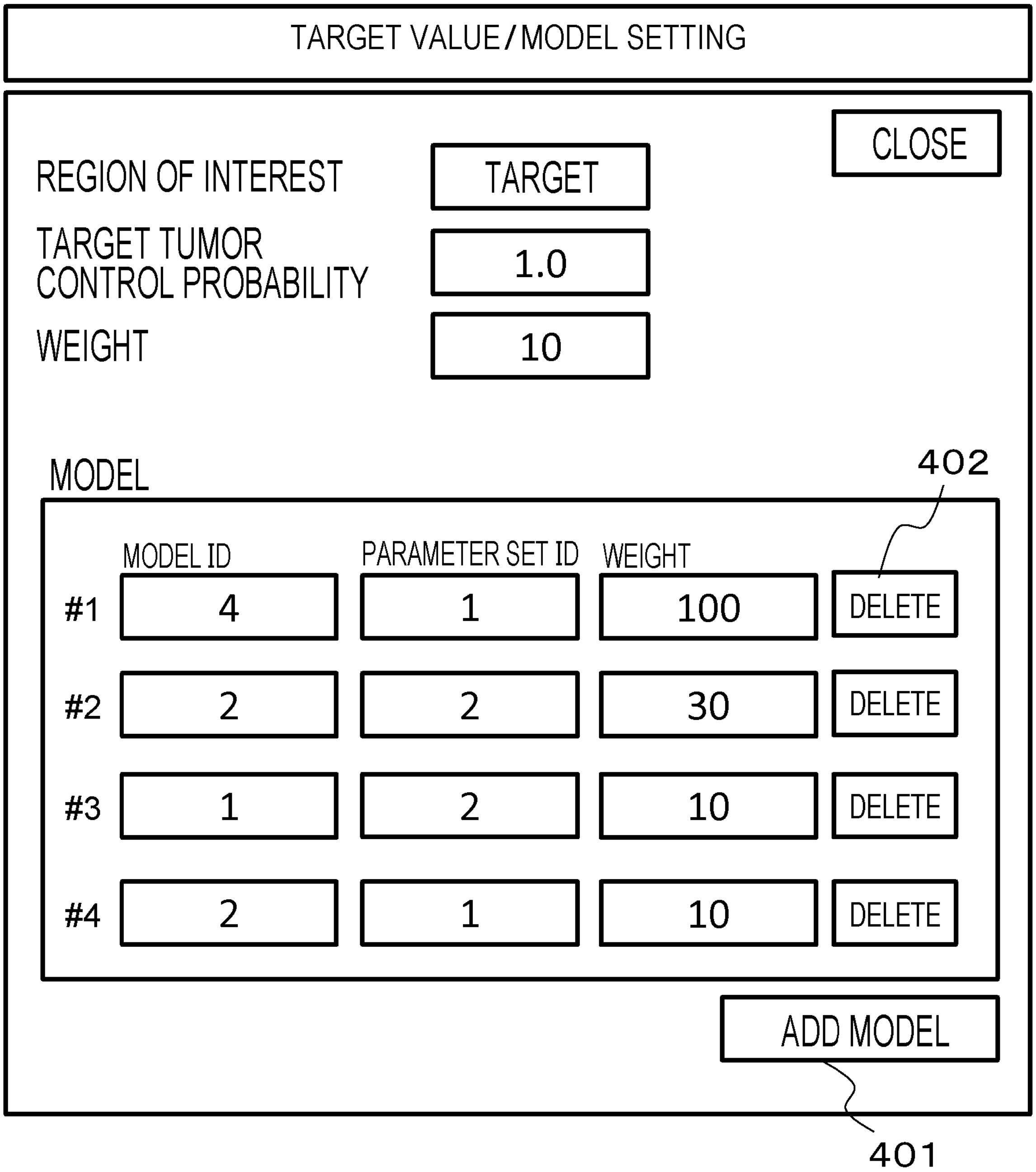
FIG. 4 is a diagram illustrating an example of a GUI for inputting a target tumor control probability, a calculation model, a weight of the model, and a parameter set used for the target region.

FIG. 4 is a diagram illustrating an example of a GUI for inputting the target tumor control probability $TCP_{obj}$ used for the target region 301 by the operator, the calculation model for the TCP, the weight $w_{model}$ of the model, and the parameter set. The operator can call the GUI illustrated in FIG. 4 for each region of interest by selecting a setting screen call button 303 for the target region illustrated in FIG. 3 using the input device 102. As illustrated in FIG. 4, a plurality of calculation models can be set for one region of interest. Note that, in the present embodiment, a plurality of different parameter sets can be combined for the same calculation model and registered in the treatment planning system 100 as separate calculation models.

The calculation model and the parameter set can be selected by the operator from a list of calculation models and parameter sets previously stored in the database 105. When the operator selects a model addition button 401 illustrated in FIG. 4, a model selection screen (FIG. 5) to be described later is called. A calculation model once added can be deleted by selecting a model deletion button 402.

Figure 5:
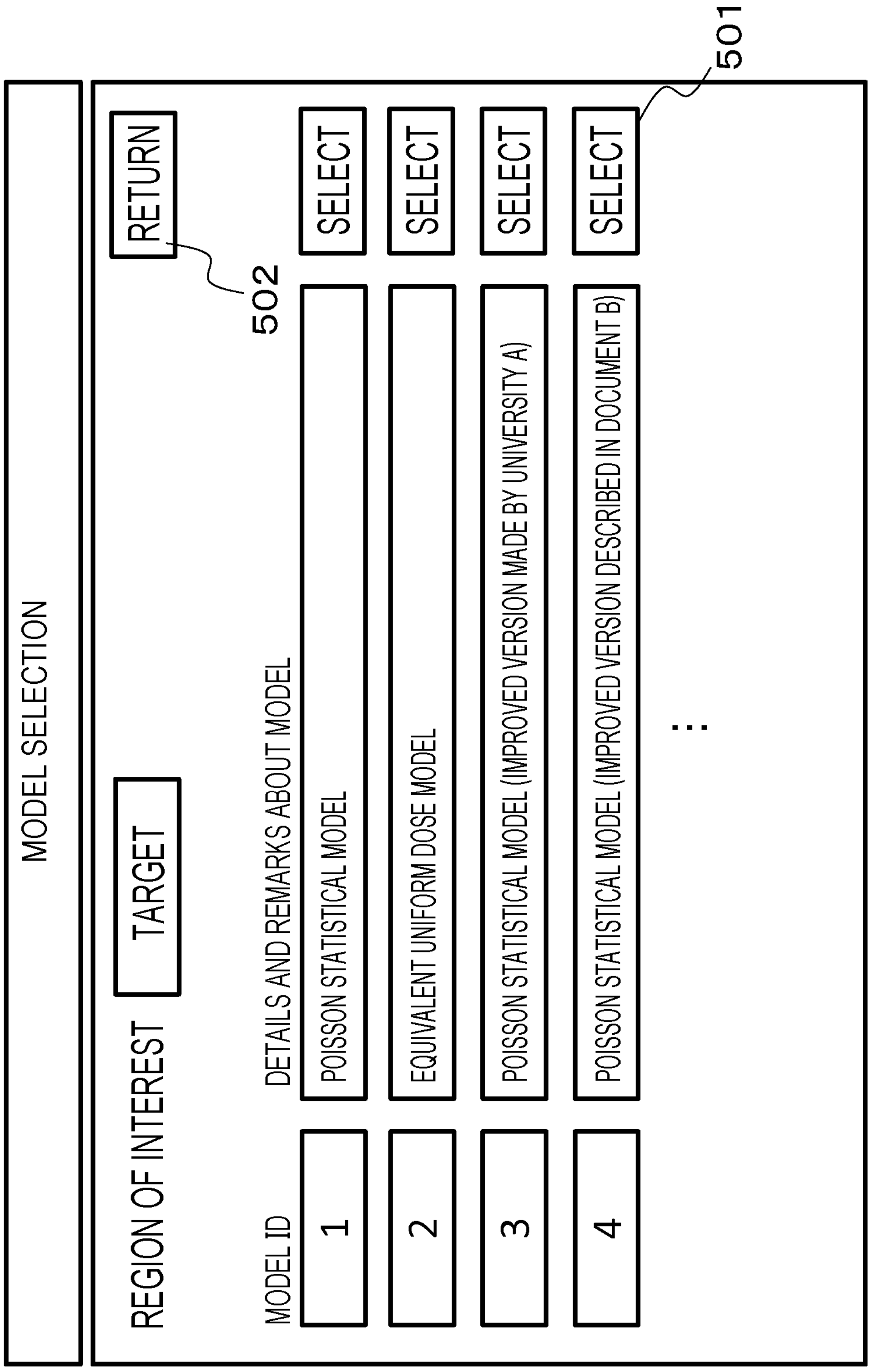
FIG. 5 is a diagram illustrating an example of a GUI for selecting a calculation model.

FIG. 5 is a diagram illustrating an example of a GUI for selecting a calculation model. A list of calculation models matching the designated type of region of interest (target, OAR) stored in the database 105 in advance is shown. By selecting a model selection button 501, the operator can select a calculation model to be newly added. After selecting a model selection cancel button (return button) 502, the operator can cancel the selection of the calculation model and return to a setting screen illustrated in FIG. 4. When the calculation model is selected in FIG. 5, a screen for selecting a parameter set is called.

Figure 6:
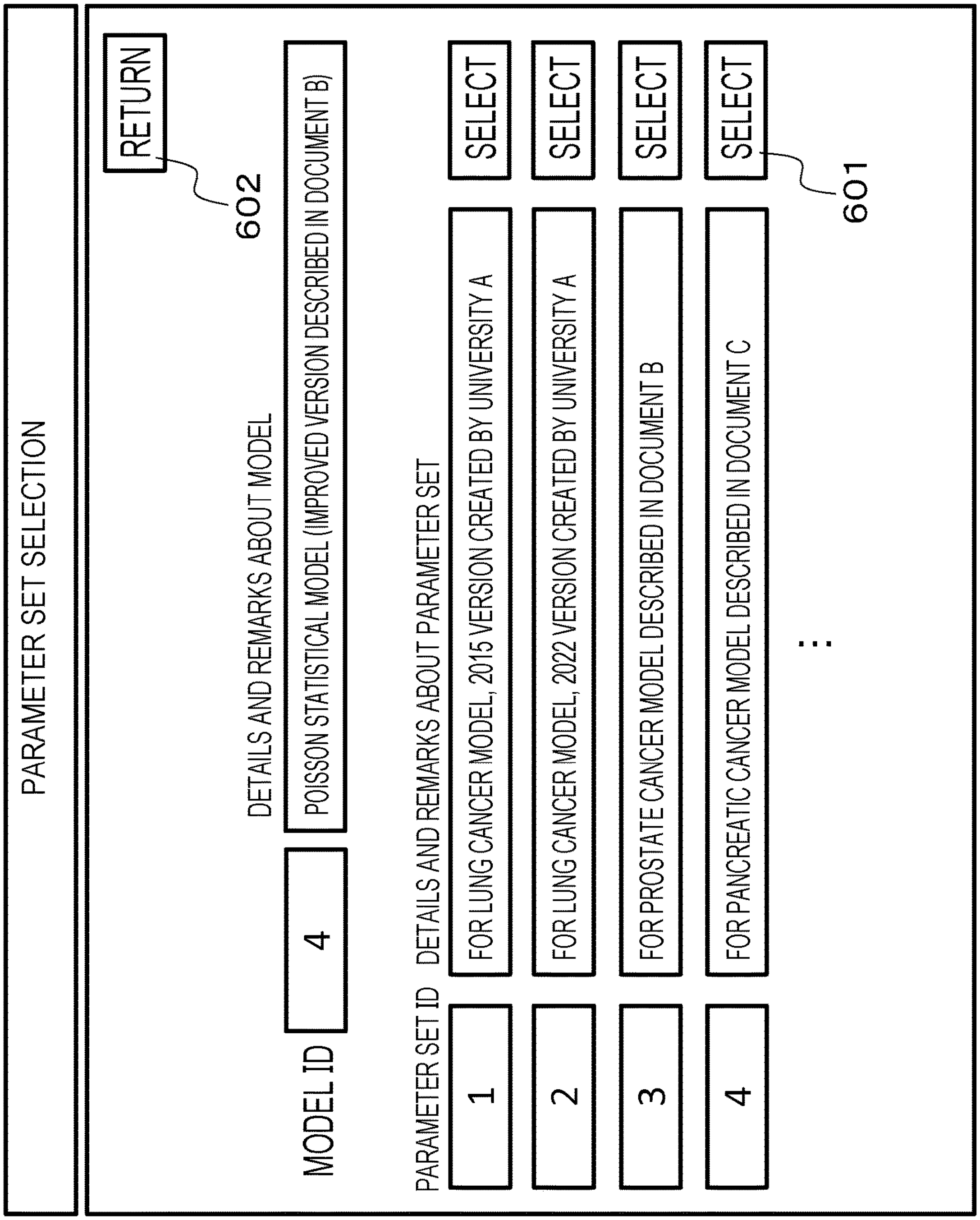
FIG. 6 is a diagram illustrating an example of a GUI for selecting a parameter set.

FIG. 6 is a diagram illustrating an example of a GUI for selecting a parameter set. In this GUI, a list of parameter sets corresponding to calculation models selected on the model selection screen illustrated in FIG. 5 among parameter sets stored in the database 105 in advance is shown. By selecting a parameter set selection button 601, the operator can select a parameter set to be used for the selected calculation model. When a parameter set selection cancel button (return button) 602 is selected, it is possible to cancel the selection of a parameter set and return to the model selection screen illustrated in FIG. 5.

The procedure in which the operator inputs the target tumor control probability $TCP_{obj}$ used for the target region 301, the calculation model for the TCP, the weight $w_{model}$ of the model, and the parameter set has been described above with reference to FIGS. 4 to 6. However, a procedure in which the operator inputs the target normal tissue complication probability $NTCP_{obj}$ of the OAR 302, the calculation model for the NTCP, the weight $w_{model}$ of the calculation model, and the parameter set of the calculation model is similar thereto. By selecting a setting screen call button 305 for the OAR illustrated in FIG. 3, a GUI for inputting the target tumor control probability $TCP_{obj}$ used for the target region 301 by the operator, the calculation model for the TCP, the weight $w_{model}$ of the model, and the parameter set is called. This GUI is similar to the GUI illustrated in FIG. 4, and the target normal tissue complication probability $NTCP_{obj}$ of the OAR 302, the calculation model for the NTCP, the weight $w_{model}$ Of the calculation model, and the parameter set of the calculation model can be input from similar GUIs to those illustrated in FIGS. 4 to 6.

When the model setting is completed for all regions of interest, the operator selects an optimization start button 304 illustrated in FIG. 3. When the optimization start button 304 is selected, a search for an optimal prescription using the set biological effect index, calculation model, weight of the model, and parameter set is started.

The description returns to FIG. 2 again.

The arithmetic processing device 101 sets an objective function for the prescription search based on the information recorded in the memory 104 or the database 105 (step S7). The objective function is expressed by Equation (3).

[Equation 3]

$$\text{Objective function}(\vec{x}, N) = w_{TCP}\sum_i w_{model}^{(i)}\left(TCP_{obj} - TCP^{(i)}\right)^2\theta\left(TCP_{obj} - TCP^{(i)}\right) + w_{NTCP}\sum_j w_{model}^{(j)}\left(NTCP_{obj} - NTCP^{(j)}\right)^2\theta\left(NTCP^{(j)} - NTCP_{obj}\right) \tag{3}$$

N and $\vec{x}$ are parameters for optimization, and are vectors having elements indicating the number of times that fractionated irradiation with radiation is performed, and an irradiation dose to each spot, respectively.

i indicates a number of a model set in the target region 301, and $w^{(i)}$ model indicates a weight of the model i.

TCP (i) indicates a tumor control probability calculated by the calculation model i.

j indicates a number of a model set in the OAR 302, and $w^{(j)}_{model}$ indicates a weight of the model j.

NTCP (j) indicates a normal tissue complication probability calculated by the calculation model j.

A function θ is a step function. In a case where an argument is positive, the function is 1, and in a case where the argument is not positive, the function is 0.

Next, as an example of a TCP calculation method by the arithmetic processing device 101, a Poisson statistical model will be described as an example of a model. It is known that the probability of cancer cells having received radiation follows Poisson statistics. Therefore, the probability $P_k$ (χ=0) that the number of cancer cells included in a voxel k in the target region 301 will be 0 at the end of treatment is expressed by Equation (4).

[Equation 4]

$$P_k(\chi=0)=\frac{\exp\{-\lambda_k n_k\}(-\lambda_k n_k)^\chi}{\chi!}=\exp\{-\lambda_k n_k\} \tag{4}$$

In this case, the survival probability $\lambda_k$ of the cancer cells in the voxel k associated with radiotherapy is expressed by a linear-quadratic curve model (LQ model) as in Equation (5).

[Equation 5]

$$\lambda_k=\exp\left\{-\alpha_i D_k\left(1+\frac{\beta_i}{N\alpha_i}D_k\right)\right\} \tag{5}$$

$D_k$ is the total irradiation dose to the voxel k, and N is the number of times that fractionated irradiation is performed. $\alpha_i$ and $\beta_i$ are parameters of a model i indicating the radiosensitivity of the cancer cells.

Since the TCP is a probability that the number of cancer cells included in the target region 301 will be 0 after the end of treatment, it is calculated by calculating the product of the probabilities P ($\chi$=0) for all voxels included in the target region 301 as in Equation (6).

[Equation 6]

$$TCP^{(i)}=\prod_k \exp\{-\lambda_k n_k\} \tag{6}$$

In the present embodiment, the TCP calculation method using the Poisson statistical model has been exemplified, but another model such as an equivalent uniform dose model can be used, and in that case, the same effect as that of the present embodiment can be obtained.

Next, an example of a method of calculating the NTCP by the arithmetic processing device 101 will be described. According to a representative model, the NTCP of the OAR is calculated according to Equation (7).

[Equation 7]

$$NTCP^{(j)}=\frac{1}{2}\left[1-\mathrm{erf}\left(\frac{t}{\sqrt{2}}\right)\right] \tag{7}$$

Here, t is expressed by Equation (8).

[Equation 8]

$$t=\frac{D_{max}v^{np}-TD_{50}}{m_p TD_{50}} \tag{8}$$

Furthermore, $D_{max}V^{np}$ is expressed by Equation (9).

[Equation 9]

$$D_{max}V^{np}=\sum_k\left\{(D_k')^{\frac{1}{np}}\frac{v}{V}\right\}^{np} \tag{9}$$

Here, V represents the volume of the entire OAR, and v represents the volume per voxel. k is a number of a voxel included in the OAR. $n_p$, $m_p$, and $TD_{50}$ are parameters determined based on past clinical data and the like, and are stored in advance in the database 105 by the operator.

$$D_k'$$

is the converted total irradiation dose to the voxel k, and indicates the total irradiation dose for obtaining the biological effect equivalent to the irradiation in which the total irradiation dose is $D_k$ and the number of times that fractionated irradiation is performed is N in a case where an irradiation dose for irradiation performed one time is $d_{ref}$=2 Gy. As described above, the probability $\lambda_k$ that normal tissue included in the voxel k survives by the irradiation in which the total irradiation dose is $D_k$ and the number of times that fractionated irradiation is performed is N can be expressed by Equation (10).

[Equation 10]

$$\lambda_k=\exp\left\{-\alpha_j D_k\left(1+\frac{\beta_j}{N\alpha_j}D_k\right)\right\} \tag{10}$$

Here, $\alpha_j$ and $\beta_j$ are parameters of a calculation model j indicating radiosensitivity of normal tissue cells. Therefore, the converted total irradiation dose $D_k'$ can be obtained as in the Equations (11) and (12).

[Equation 11]

$$\lambda_k=\exp\left\{-\alpha_j D_k\left(1+\frac{\beta_j}{N\alpha_j}D_k\right)\right\}=\exp\left\{-\alpha_j N_{ref}d_{ref}\left(1+\frac{\beta_j}{\alpha_j}d_{ref}\right)\right\} \tag{11}$$

$$D_k'=N_{ref}d_{ref}=D_k\frac{\alpha_j+\beta_j D_k/N}{\alpha_j+\beta_j d_{ref}} \tag{12}$$

Note that the NTCP calculation method described in the present embodiment is an example, and it is also possible to calculate the NTCP using another model equation, and in that case, the same effect as that of the present embodiment can be obtained.

The dose $D_k$ for each voxel obtained in the calculation of the TCP and the NTCP is calculated based on Equation (13) indicating the relationship between a vector (hereinafter, also referred to as an absorbed dose vector) having the absorbed dose of each voxel included in the target region 301 and the OAR 302 as an element and a vector (hereinafter, also referred to as a spot dose vector) having a beam dose to each spot as an element.

[Equation 12]

$$\vec{D_k}=A\vec{x} \tag{13}$$

$\vec{D}_k$ is the absorbed dose vector, and $\vec{x}$ is the spot dose vector.

A matrix A is a matrix representing the dose given to each voxel k by radiation applied to each spot, and is calculated based on an irradiation direction set in advance by the operator and in-vivo information of a CT image.

The description returns to FIG. 2 again. When the objective function is generated in step S7, the arithmetic processing device 101 obtains an irradiation dose to each spot and the number of times that fractionated irradiation is performed that minimize the objective function by iterative search (step S8). The end condition is not particularly limited, but a condition according to an index may be set using, as the index, the total calculation time of iterative calculation in iterative search, the number of iterations of the calculation in the iterative search, the amount of a change in the objective function per iteration in the iterative calculation, or the like.

The absorbed dose vector indicated on the left side of Equation (13) can be estimated based on the assumption that the dose in the target region 301 is $D_{mean}$ and is uniformly distributed and isotropically decreases outside the target according to the distance from the target region 301 even when the spot dose vector included on the right side of Equation (13) is unknown. Under this assumption, the dose $D_{mean}$ can be used as a search parameter instead of the spot dose vector. As a result, since the number of search parameters is reduced, fast convergence can be expected. However, after the search for the number N of times that fractionated irradiation is performed and the central dose $D_{mean}$ is completed, a procedure for determining a spot dose vector again based on an objective function F' expressed in Equation (14) is required.

[Equation 13]

$$F'^{(\vec{x})} = \sum_k (D_{mean} - D_k)^2 \tag{14}$$

However, the relationship between the absorbed dose vector and the spot dose vector is as expressed in Equation (13).

The description returns to FIG. 2 again. Finally, the arithmetic processing device 101 calculates a three-dimensional dose distribution based on the obtained beam dose to each spot, displays the calculation result on the display device 103, records the calculation result in the memory 104 or the database 105, and completes the treatment planning (step S9).

The embodiments described above are examples for describing the present invention, and are not intended to limit the scope of the present invention only to those embodiments. A person skilled in the art can implement the present invention in various other aspects without departing from the scope of the present invention. In addition, the above-described embodiment includes the following items. However, the items included in the present embodiment are not limited to the following items.

(Item 1)

A treatment planning system is configured to create a treatment planning for radiotherapy, and includes a memory configured to store a plurality of calculation models, and a processing device configured to calculate calculation values of biological effect indices representing an effect of radiotherapy with respect to a condition for the radiotherapy using at least two of the plurality of calculation models, and search for the condition so that at least two of the calculation values to be calculated approach a predetermined target value.

According to this, since the condition is searched so that the calculation values of the biological effect indices calculated using two or more calculation models approach the target value, it is possible to create a robust treatment planning independent of one calculation model and a parameter set.

(Item 2)

In the treatment planning system described in Item 1, the processing device searches for the condition using an objective function based on a difference between the calculation values and the target value. Therefore, the condition can be searched by the optimization of the objective function.

(Item 3)

In the treatment planning system described in Item 2, the objective function is a function that weights the difference between the calculation values and the target value by a weight specified for the at least two calculation models so as to add the weight to the difference. According to this, it is possible to optimize prescription by giving priority to each calculation model.

(Item 4)

In the treatment planning system described in Item 3, the processing device searches for the condition so as to minimize a value of the objective function.

(Item 5)

In the treatment planning system described in Item 1, the processing device calculates the biological effect indices for a target region to be irradiated with radiation and/or a risk region not to be irradiated with the radiation in radiotherapy.

(Item 6)

In the treatment planning system described in Item 5, the biological effect indices are a tumor control probability of the target region and a normal tissue complication probability of the risk region. According to this, it is possible to search for a prescription that optimizes the tumor control probability and the normal tissue complication probability.

(Item 7)

In the treatment planning system described in Item 1, the condition includes the number of times that fractionated irradiation is performed and an irradiation dose to each spot in spot scanning irradiation. This makes it possible to search for the optimum number of times that fractionated irradiation is performed and the irradiation dose to each spot.

(Item 8)

The treatment planning system described in Item 1 further includes a display device, and the processing device displays, on the display device, a management screen indicating information regarding the at least two calculation models used for calculation of the biological effect indices. According to this, a treatment planning creator can create the treatment planning while confirming which calculation model to use.

(Item 9)

In the treatment planning system described in Item 8, the processing device displays, on the display device, a selection screen that enables selection of a calculation model that is among the plurality of calculation models stored in the memory and is to be used for the calculation of the biological effect indices. According to this, the treatment planning creator can select a calculation model on the selection screen and create the treatment plan.

(Item 10)

The treatment planning system according to claim 5 further includes a display device, and the processing device displays, on the display device, a management screen indicating information regarding the at least two calculation models used for calculation of the biological effect indices, in association with a region of interest for which the biological effect indices are calculated. According to this, the treatment planning creator can create the treatment planning while confirming the region of interest and the calculation model on the screen.

What is claimed is:

1. A treatment planning system configured to create a treatment planning for radiotherapy, the treatment planning system comprising:

a memory configured to store a plurality of calculation models; and a processing device configured to:

calculate calculation values of biological effect indices representing an effect of radiotherapy with respect to a condition for the radiotherapy using at least two of the plurality of calculation models, search for the condition so that at least two of the calculation values to be calculated approach a predetermined target value, wherein the processing device searches for the condition using an objective function based on a difference between the calculation values and the target value, wherein the objective function is a function that weights the difference between the calculation values and the target value by a weight specified for the at least two calculation models so as to add the weight to the difference, and wherein the processing device searches for the condition so as to minimize a value of the objective function.

2. The treatment planning system according to claim 1, wherein the processing device calculates the biological effect indices for a target region to be irradiated with radiation and/or a risk region not to be irradiated with the radiation in radiotherapy.

3. The treatment planning system according to claim 2, wherein the biological effect indices are a tumor control probability of the target region and a normal tissue complication probability of the risk region.

4. The treatment planning system according to claim 1, wherein the condition includes a number of times that fractionated irradiation is performed and an irradiation dose to each spot in spot scanning irradiation.

5. The treatment planning system according to claim 1, further comprising a display device, wherein the processing device displays, on the display device, a management screen indicating information regarding the at least two calculation models used for calculation of the biological effect indices.

6. The treatment planning system according to claim 5, wherein the processing device displays, on the display device, a selection screen that enables selection of a calculation model that is among the plurality of calculation models stored in the memory and is to be used for the calculation of the biological effect indices.

7. The treatment planning system according to claim 2, further comprising a display device, wherein the processing device displays, on the display device, a management screen indicating information regarding the at least two calculation models used for calculation of the biological effect indices, in association with a region of interest for which the biological effect indices are calculated.

8. A treatment planning method for creating a treatment planning for radiotherapy by a treatment planning system including a processing device and a memory, the treatment planning method comprising:

causing the processing device to store a plurality of calculation models to the memory;

causing the processing device to calculate calculation values of biological effect indices representing an effect of radiotherapy with respect to a condition for the radiotherapy using at least two of the plurality of calculation models; and causing the processing device to search for the condition so that at least two of the calculation values to be calculated approach a predetermined target value, wherein the processing device searches for the condition using an objective function based on a difference between the calculation values and the target value, wherein the objective function is a function that weights the difference between the calculation values and the target value by a weight specified for the at least two calculation models so as to add the weight to the difference, and wherein the processing device searches for the condition so as to minimize a value of the objective function.

9. A non-transitory computer readable medium storing thereon a treatment planning program for creating a treatment planning for radiotherapy by a treatment planning system including a processing device and a memory, the treatment planning program causing the processing device to:

store a plurality of calculation models to the memory; and calculate calculation values of biological effect indices representing an effect of radiotherapy with respect to a condition for the radiotherapy using at least two of the plurality of calculation models; and search for the condition so that at least two of the calculation values to be calculated approach a predetermined target value, wherein the processing device searches for the condition using an objective function based on a difference between the calculation values and the target value, wherein the objective function is a function that weights the difference between the calculation values and the target value by a weight specified for the at least two calculation models so as to add the weight to the difference, and wherein the processing device searches for the condition so as to minimize a value of the objective function.

10. The treatment planning system according to claim 1, wherein the memory is configured to store a first plurality of combinations of relationships between tumor control probability (TCP), first calculation models, weights of the first calculation models, and first parameter sets and a second plurality of combinations of relationships between normal tissue complication probability (NTCP), second calculation models, weights of the second calculation models, and second parameter sets, and the processing device selects a preferred combination of one of the first plurality of combinations and one of the second plurality of combinations so as to minimize a value of the objective function.

11. The treatment planning method according to claim 8, wherein the memory is configured to store a first plurality of combinations of relationships between tumor control probability (TCP), first calculation models, weights of the first calculation models, and first parameter sets and a second plurality of combinations of relationships between normal tissue complication probability (NTCP), second calculation models, weights of the second calculation models, and second parameter sets, and the processing device selects a preferred combination of one of the first plurality of combinations and one of the second plurality of combinations so as to minimize a value of the objective function.

12. The non-transitory computer readable medium according to claim 9, wherein the memory is configured to store a first plurality of combinations of relationships between tumor control probability (TCP), first calculation models, weights of the first calculation models, and first parameter sets and a second plurality of combinations of relationships between normal tissue complication probability (NTCP), second calculation models, weights of the second calculation models, and second parameter sets, and the processing device selects a preferred combination of one of the first plurality of combinations and one of the second plurality of combinations so as to minimize a value of the objective function.

* * * * *